United States Patent [19]

Beau et al.

[11] Patent Number: 5,405,948
[45] Date of Patent: Apr. 11, 1995

[54] 1,5-DIYNE-3-CYCLOALKENE COMPOUNDS

[75] Inventors: Jean-Marie Beau, Menestreau en Villette; Christophe Crevisy, Orleans; Ghanem Atassi, Saint Cloud; Alain Pierre, Marly le Roi, all of France

[73] Assignee: Adir et Compagnie, Courbevoie, France

[21] Appl. No.: 954,004

[22] Filed: Sep. 30, 1992

Related U.S. Application Data

[63] Continuation-in-part of Ser. No. 896,160, Jun. 10, 1992, abandoned.

[30] Foreign Application Priority Data

Jun. 11, 1991 [FR] France ........................ 91.07045

[51] Int. Cl.$^6$ ................... C07H 15/24; C07C 67/02; C07C 43/20
[52] U.S. Cl. .................... 536/18.1; 560/255; 560/256; 568/659; 568/667; 568/808; 568/821; 568/326
[58] Field of Search ............ 560/255, 256; 568/659, 568/667, 808, 821, 326; 536/18.1

[56] References Cited

PUBLICATIONS

Pierre, et al., Cancer Chemotherapy and Pharmacology 29, 367–374 (1992).
Goodman and Gilman, The Pharmacological Basis of Therapeutics, 8th Edition, p. 1203.
Yamaue, et al., Eur. J. Cancer 27, No. 10, 1258–1263 (1991).
Rubenstein, et al., Journal of the National Cancer Institute 82, No. 13, 1113 (Jul. 4, 1990).
Keepers et al., Eur. J. Cancer 27, No. 7, pp. 897–900 (1991).
Carmichael, et al., Cancer Research 47, pp. 936–942 (Feb. 15, 1987).
Michael Boyd, M.D., Ph.D., "Status of the NCI Pre-clinical Antitumor Drug Discovery Screen", Principles and Practice of Oncology 3, No. 10, (Oct. 1989).
Alley, et al., Cancer Research 48, pp. 589–601 (Feb. 1, 1988).
B. Long et al., Proc. Natl. Acad. Sci., 86, 2–6 (1989).
M. Jarman, Nature, 349, 566–567 (1991).
K. Sonogashira et al., Tetrahedron Lett., 50, 4467–4470 (1975).
D. Guillerm, et al., Tetrahedron Lett. 26(32), 3811–3812 (1985).
K. Takai et al., Tetrahedron Lett., 26(45), 5585–5588 (1985).
T. Aicher et al., Tetrahedron Lett., 28(30), 3463–3466 (1987).
M. Alley et al., "Microculture Tetrazolium Assay", Cancer Res., 48, 589–601 (1988).

*Primary Examiner*—José G. Dees
*Assistant Examiner*—Joseph M. Conrad, III
*Attorney, Agent, or Firm*—Gordon W. Hueschen

[57] ABSTRACT

A compound of formula (I): selected from 1,5-diyne-3-cyclodecene and undecene compounds.

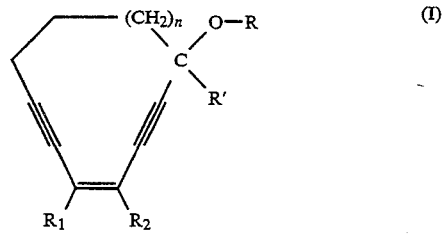

in which:
R represents a hydrogen atom, a straight-chain or branched ($C_1$–$C_6$) acyl radical or a glycoside radical,
R' represents a hydrogen atom

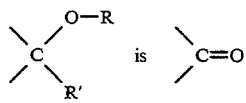

n is 1 or 2, and
$R_1$ and $R_2$ simultaneously represent two hydrogen atoms or, together with the two carbon atoms and the double bond to which they are attached, form a phenyl ring.

4 Claims, No Drawings

1,5-DIYNE-3-CYCLOALKENE COMPOUNDS

The present application is a continuation-in-part of our prior-filed application Ser. No. 07/896,260, filed Jun. 10,1992, now abandoned.

The present invention relates to new 1,5-diyne-3-cycloalkene compounds.

Esperamicins and calicheamicins belong to two families of natural antibiotics possessing anti-tumor properties which are distinctly more powerful than those of the known anti-cancer compounds described by B. LONG et al. (Proc. Natl. Acad. Sci., 86, 2–6, 1989).

The anti-tumor properties of the two series of compounds are due to the presence of a 1,5-diyne-3-cycloalkene ring common to these two families (Nature, 349, 566–567, 1991).

The present invention relates to 1,5-diyne-3-cycloalkene compounds which, in addition to the fact that they are novel, have particularly intense anti-tumor properties.

The invention relates more particularly to novel 1,5-diyne-3-cycloalkene compounds corresponding to the general formula (I):

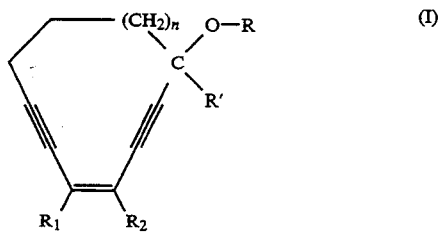

in which:
R represents a hydrogen atom, a straight-chain or branched ($C_1$–$C_6$) acyl radical or a glycoside radical,
R' represents a hydrogen atom

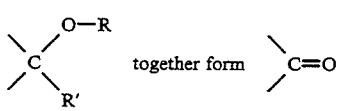

n is 1 or 2, and
$R_1$ and $R_2$ simultaneously represent two hydrogen atoms or, together with the double bond to which they are attached, form a phenyl ring,
their isomers and enantiomers.

The invention also extends to the process for the preparation of the compounds of formula (I), characterised in that (Z)-1,2-dichloroethylene or 1,2-dibromobenzene is reacted in an anhydrous medium, under an inert atmosphere, with an alcohol of formula (II):

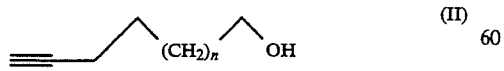

in which n has the same meaning as in formula (I), in the presence of a palladium catalyst prepared from tetrakis(triphenylphosphine)palladium, n-propylamine and copper iodide, in accordance with the techniques described by K. SONOGASHIRA et al. (Tetrahedron lett. 4467–4470, 1975) and D. GUILLERM (Tetrahedron lett., 26, 3811–3812, 1985), to lead to the compound of formula (III)

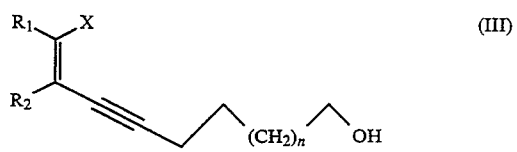

in which n, $R_1$ and $R_2$ have the same meaning as in formula (I) and X represents a chlorine or bromine atom depending on the starting material used, which compound is coupled, as above, in the presence of tetrakis(triphenylphosphine)palladium, n-propylamine and copper iodide, with trimethylsilylacetylene, in an anhydrous medium, under an inert atmosphere, to lead to the compound of formula (IV):

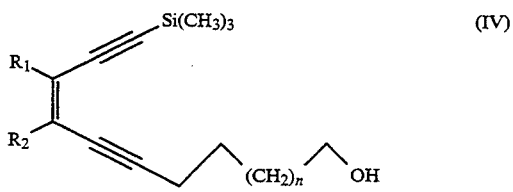

in which n, $R_1$ and $R_2$ have the same meaning as in formula (I), which compound is subjected to a desilylation in an anhydrous basic medium, under an inert atmosphere, to lead to the compound of formula (V):

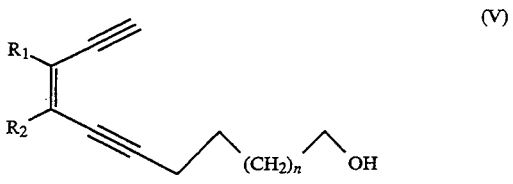

in which n, $R_1$ and $R_2$ have the same meaning as in formula (I), with which iodine is reacted, in an anhydrous organic medium in the presence of morpholine, under an inert atmosphere, to lead to the compound of formula (VI):

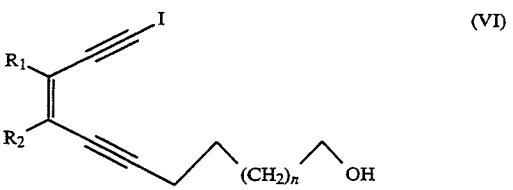

in which n, $R_1$ and $R_2$ have the same meaning as in formula (I), which compound is subjected to oxidation in the presence of pyridinium chlorochromate in an anhydrous organic medium, under an inert atmosphere, to lead to the compound of formula (VII):

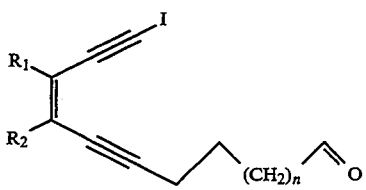

(VII)

in which n, $R_1$ and $R_2$ have the same meaning as in formula (I), which is cyclised with the aid of a mixture of chromium chloride containing 1.3% of nickel chloride in suspension in anhydrous tetrahydrofuran, at ambient temperature, under an inert atmosphere, in accordance with the techniques described by K. TAKAI et al., (Tetrahedron lett., 26, 5585–5588, 1985) and T. D. AICHER (Tetrahedron lett., 28, 3463–3466, 1987), to lead to the compound of formula (I/a), a particular case of the compounds of formula (I):

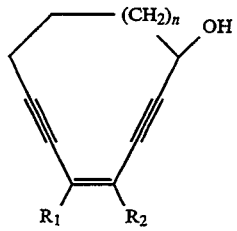

(I/a)

in which n has the same meaning as in formula (I), which compound is:

either converted to the corresponding ester, under an inert atmosphere, to lead to the compound of formula (I/b), a particular case of compounds of formula (I),

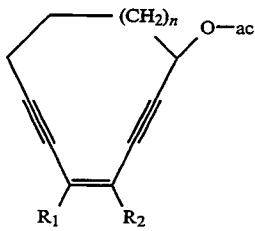

(I/b)

in which n, $R_1$ and $R_2$ have the same meaning as in formula (I), and ac represents a straight-chain or branched ($C_1$–$C_6$) acyl group, or oxidized in the presence of pyridinium chlorochromate, to lead to the compound of formula (I/c), a particular case of the compounds of formula (I),

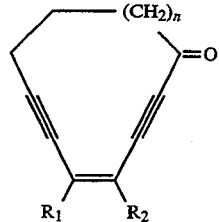

(I/c)

in which n, $R_1$ and $R_2$ have the same meaning as in formula (I), or glycosylated in the presence of acetyl glycoside trichloroacetamidate and then deacetylated after separating the isomers if appropriate, to lead to the compound of formula (I/d), a particular case of the compounds of formula (I),

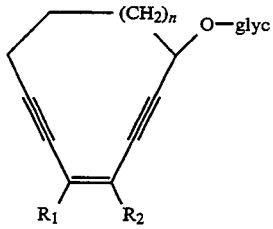

(I/d)

in which n, $R_1$ and $R_2$ have the same meaning as in formula (I) and glyc represents a glycoside group, which compounds of formula (I/a), (I/b), (I/c) and (I/d) are purified, if necessary, using a conventional preparation technique and the isomers of said compounds being separated, if desired, using a conventional separation technique.

The compounds of the invention have very valuable pharmacological properties. They inhibit the proliferation of L 1210 (murine leukaemia) cells in culture, which is predicative of a good anti-tumor activity in animals and also in man.

The present invention also relates to the pharmaceutical compositions containing, as active principle, at least one compound of general formula (I) or one of its addition salts with a pharmaceutically acceptable acid, on its own or in combination with one or more non-toxic, inert excipients or vehicles.

Amongst the pharmaceutical compositions according to the invention, those which may be mentioned more particularly are those which are suitable for oral, parenteral or nasal administration, simple or coated tablets, sublingual tablets, capsules, suppositories, creams, ointments, dermal gels and aerosols.

The dosage varies depending on the age and the weight of the patient, the nature and the severity of the disease and the mode of administration. The latter may be oral, nasal, rectal or parenteral. In general, the dosage ranges between 0.2 and 200 mg for a treatment taken in one or more doses per 24 hours.

The following examples illustrate the invention and do not limit it in any way.

EXAMPLE 1:

1,5-diyne-(3Z)-cyclodecen-7-ol

Stage A: 8-chloro-5-yne-7-octen-1-ol

650 μl (7.01 mmol) of n-propylamine, 480 μl (4.26 mmol) of 5-hexyn-1-ol, 420 μl (5.40 mmol) of cis-dichloroethylene and 35 mg (0.184 mmol) of copper iodide are added successively to a solution of 85 mg (0.074 mmol) of tetrakis(triphenylphosphine)palladium in 8 ml of anhydrous benzene. The reaction mixture is heated for 100 minutes at 40° C. under an inert atmosphere, then concentrated and taken up in diethyl ether. The organic phase is washed with a saturated aqueous solution of sodium chloride, dried and then evaporated. The expected product is obtained in the form of a colourless liquid after purification by chromatography on silica using a (40/1) dichloromethane/acetone mixture as elution solvent.

Yield: 78% Mass spectrum: chemical ionisation ($NH_3$) M+$NH_4$: m/z=176

Stage B: 10-trimethylsilyl-5,9-diyne-7-decen-1-ol 516 mg (3.25 mmol) of the compound obtained in stage A, in 7 ml of anhydrous benzene, are treated with 500 μl (6.08 mmol) of n-propylamine, 70 mg (0.061 mmol) of tetrakis(triphenylphosphine)palladium, 32 mg (0.168 mmol) of copper iodide and 650 μl (4.51 mmol) of trimethylsilylacetylene. The reaction mixture is stirred for 100 minutes at ambient temperature, under an inert atmosphere, then concentrated and taken up in diethyl ether. The organic phase is washed with a saturated aqueous solution of sodium chloride and then with water, dried and evaporated. The expected product is obtained, in the form of an oil, after purification by liquid chromatography on silica using a (40/1/0.04) dichloromethane/acetone/triethylamine mixture as elution solvent.

Yield: 82%

Stage C: 5,9-diyne-7-decen-1-ol 1.12 g (5.08 mmol) of the compound obtained in stage B, in solution in 10 ml of anhydrous methanol, are treated with 770 mg (5.57 mmol) of potassium carbonate at ambient temperature, under an inert atmosphere, for 15 minutes. The reaction mixture is then concentrated, taken up in dichloromethane and washed with water. The organic phase is then dried and evaporated. The expected product is obtained, in the form of a colourless oil, after purification by liquid chromatography on silica using a (20/1) dichloromethane/acetone mixture as elution solvent.

Yield: 90% Mass spectrum: chemical ionisation (NH$_3$) M+NH$_4^+$: m/z=166

Stage D: 10-iodo-5,9-diyne-7-decen-1-ol 2.49 ml (28.55 mmol) of morpholine are added to a solution containing 2.42 g (9.53 mmol) of iodine in 20 ml of anhydrous benzene heated to 45° C. After stirring for 20 minutes at 45° C., under an inert atmosphere, 675 mg (4.55 mmol) of the compound obtained in stage C, in solution in 5 ml of anhydrous benzene, are added. The reaction mixture is stirred for a further 3 hours at 45° C., concentrated, taken up in diethyl ether and washed successively with a saturated aqueous solution of sodium chloride, a 20% aqueous solution of sodium dihydrogen phosphate, a 20% aqueous solution of sodium thiosulfate, a 10% aqueous solution of sodium bicarbonate and then with water. The organic phase is then washed and evaporated. The expected product is then obtained, in the form of an oil, after purification by chromatography on silica using a (1/1) hexane/diethyl ether mixture as elution solvent.

Yield: 80% Mass spectrum: Chemical ionisation (NH$_3$) M+NH$_4^+$: m/z=292

Stage E: 10-iodo-5,9-diyne-7-decen-1-al 250 mg (1.16 mmol) of pyridinium chlorochromate and 2 ml of dichloromethane are stirred in activated molecular sieve (4 Å) in powder form for 20 minutes, at ambient temperature, under an inert atmosphere. 94 mg (0.343 mmol) of the compound obtained in stage D, in solution in 3 ml of anhydrous dichloromethane, are added to the above mixture. The mixture is stirred for a further 30 minutes at ambient temperature and 20 ml of diethyl ether are then added. The reaction mixture is then filtered and then concentrated. The expected product is obtained after purification by chromatography on silica using a (1/1) hexane/diethyl ether mixture as elution solvent.

Yield: 83% Mass spectrum: Chemical ionisation (NH$_3$) M+NH$_4^+$: m/z=290

Stage F: 1,5-diyne-3-cyclodecen-7-ol 181 mg (1.47 mmol) of chromium chloride containing 1.3% of nickel chloride in suspension in 20 ml of tetrahydrofuran are stirred for 20 minutes at ambient temperature, under an inert atmosphere. 78 mg (0.29 mmol) of the compound obtained in stage E, in solution in 9 ml of tetrahydrofuran, are added very slowly to the above mixture. After the addition, which takes about 2 hours 40 minutes, the reaction mixture is concentrated and taken up in ethyl acetate. The organic phase is washed with a saturated aqueous solution of sodium chloride, dried and then evaporated. The expected product is obtained in the form of an oil after purification by liquid chromatography on silica using a (75/25/0.1) hexane/ethyl acetate/triethylamine mixture as elution solvent.

Yield: 34% Mass spectrum: Chemical ionisation (NH$_3$) M+NH$_4^+$: m/z=164

EXAMPLE 2:

7-acetoxy-1,5-diyne-3-cyclodecene 14.6 mg (0.1 mmol) of the compound obtained in Example 1 are treated with 1 ml of pyridine and 0.5 ml of acetic anhydride for 45 minutes, at ambient temperature, under an inert atmosphere. The reaction mixture is diluted with diethyl ether and washed successively with water, a 50% aqueous solution of potassium hydrogen sulfate, a 50% aqueous solution of sodium bicarbonate and then with water. The organic phase is dried and then evaporated. The expected product is obtained in the form of an oil after purification by liquid chromatography on silica using a (83/17/0.1) hexane/ethyl acetate/triethylamine mixture as elution solvent.

Yield: 59% Mass spectrum: Electronic impact M: m/z=188

EXAMPLE 3:

1,5-diyne-3-cycloundecen-7-ol

The expected product is obtained by following the procedure as in Example 1 but using 6-heptyn-1-ol in place of 5-hexyn-1-ol in stage A.

Yield (stage F): 76% Mass spectrum: Chemical ionisation (NH$_3$) M+NH$_4^+$: m/z=178

EXAMPLE 4:

7-acetoxy-1,5-diyne-3-cycloundecene

The expected product is obtained by following the procedure as in Example 2 but replacing the compound of Example 1 by the compound of Example 3.

Yield: 90% Mass spectrum: Electronic impact M: m/z=202

EXAMPLE 5:

7-hydroxy-benzo[c]cyclodeca-1,5-diyne

The expected product is obtained by following the procedure as in Example 1 but replacing cis-dichloroethylene by 1,2-dibromobenzene in stage A.

Mass spectrum: Electronic impact M: m/z=196

EXAMPLE 6:

7-acetoxy-benzo[c]cyclodeca-1,5-diyne

The expected product is obtained by following the procedure as in Example 2 but replacing the compound of Example 1 by the compound of Example 5.

Yield: 70% Mass spectrum: Electronic impact M: m/z=238

EXAMPLE 7:

7-oxo-benzo[c]cyclodeca-1,5-diyne

The expected product is obtained by oxidation of the compound of Example 5 in the presence of pyridinium chlorochromate.

Yield: 70% Mass spectrum: Electronic impact M: m/z=194

EXAMPLE 8:

7-($\beta$-D-glucopyranosyl)benzo[e]cyclodeca-1,5-diyne, isomer 1 and

EXAMPLE 9:

7-($\beta$-D-glucopyranosyl)benzo[c]cyclodeca-1,5-diyne, isomer 2

EXAMPLE 8:

7-($\beta$-D-glucopyranosyl)benzo[c]cyclodeca-1,5-diyne, isomer 1

Stage A:
7-($\beta$D-2,3,4,6-tetra-O-acetylglucopyranosyl)benzo[c]cyclodeca-1,5-diyne, isomer 1

413 mmol of the compound obtained in Example 5 and of 2,3,4,6-tetra-O-acetyl-a-D-glucopyranosyl trichloroacetamidate prepared in accordance with the process described by Schmidt and Michel (Angew. Chem., Int. Ed. Engl., 19, 1980, 731–732) are stirred in 2 ml of anhydrous toluene for 3 hours under an inert atmosphere in the presence of molecular sieve (4 Å). The mixture is cooled to $-78°$ C. and 92 $\mu$l of boron trifluoride etherate in toluene are then added. After the temperature has returned to $0°$ C., the mixture is neutralized with ethyl-diisopropylamine and then filtered and the filtrate is evaporated. The expected product, isomer 1, is purified and separated from isomer 2 by chromatography on silica gel using a (3/1) hexane/ethyl acetate mixture as eluent.

Optical rotation: $[\alpha]D^{20} = -50°$ (C=1 mg/ml/CHCl$_3$)

Stage B:
7-($\beta$-D-glucopyranosyl)benzo[c]cyclodeca-1,5-diyne, isomer 1

The product obtained in the preceding stage, in solution in a (1/1) dichloromethane/methanol mixture, is treated with a catalytic amount of sodium methanolate at ambient temperature, under an inert atmosphere. The reaction mixture is then neutralized on Amberlite resin (IRC 50—H$^+$ form) and then filtered. The expected product is then obtained after filtration, evaporation of the solvent and purification by chromatography on silica gel using a (6/1) dichloromethane/methanol mixture as eluent.

Yield: 80% Melting point: 123° C. (MeOH) Optical rotation: $[\alpha]D^{20} = 18°$ C. (C=0.85 mg/ml - acetone)

EXAMPLE 9:

7-($\beta$-D-glucopyranosyl)benzo[c]cyclodeca-1,5-diyne, isomer 2

The expected product is obtained by following the procedure as in stage B of Example 8, using isomer 2 from stage A of Example 8 as the starting material.

Yield: 80% Melting point: 126° C. Optical rotation: $[\alpha]D^{20} = +77°$ (C=1.2 mg/ml - CHCl$_3$/MeOH (1/1))

PHARMACOLOGICAL STUDY OF THE DERIVATIVES OF THE INVENTION

EXAMPLE 10 in vitro cytotoxicity

L 1210 (murine leukaemia) cells are cultured in RPMI 1640 supplemented by 10% fetal calf serum, 2 mM L-glutamine, 100 units/ml penicillin, 100 $\mu$g/ml streptomycin and 10 mM Hepes (pH: 7.4). The inhibition of cell growth is determined using the "Microculture Tetrazolium Assay" described by M. ALLEY et al., (Cancer Res., 48, 589–601, 1988).

The results of this test are expressed as IC$_{50}$, the concentration resulting in 50% inhibition of cell growth. The reference product used is BCNU, a highly active alkylating agent used in medicine.

During this test, the IC$_{50}$ of the compound of Example 2 is 5.6 $\mu$M and that of the compound of Example 7 is 0.5$\mu$M, whereas that of BCNU is 6.4 $\mu$M.

PHARMACEUTICAL COMPOSITION

EXAMPLE 11

Tablet: preparation formulation for 1000 tablets containing a dose of 2 mg

| | |
|---|---|
| Compound of Example 2 | 2 g |
| Hydroxypropylcellulose | 2 g |
| Wheat starch | 10 g |
| Lactose | 100 g |
| Magnesium stearate | 3 g |
| Talc | 3 g |

We claim:

1. A compound of formula (I): selected from 1,5-diyne-3-cyclodecene and undecene compounds

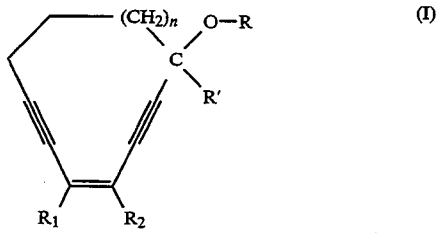

in which:
R represents hydrogen, straight-chain or branched (C$_1$-C$_6$) acyl or glycoside,
R' represents a hydrogen atom

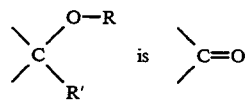

n is 1 or 2, and
R$_1$ and R$_2$ simultaneously represent two hydrogen atoms or, together with the two carbon atoms and the double bond to which they are attached, form a phenyl ring, and
their isomers and enantiomers.

2. A compound according to claim 1 wherein n is 1.
3. A compound of claim 1, selected from 7-acetoxy-1,5-diyne-3-cyclodecene, and its enantiomers.
4. The compound 7-oxo-benzocyclodeca-1,5-diyne.

* * * * *

UNITED STATES PATENT AND TRADEMARK OFFICE
CERTIFICATE OF CORRECTION

PATENT NO. : 5,405,948

DATED : April 11, 1995

INVENTOR(S) : Jean-Marie Beau, Christophe Crevisy, Ghanem Atassi, Alain Pierre

It is certified that error appears in the above-indentified patent and that said Letters Patent is hereby corrected as shown below:

TITLE PAGE, ITEM [56] LINE 9; "Rubenstein" should read
-- Rubinstein --

Column 1, line 5; insert the word "copending" between the words "filed" and "application" also "07/896,260" should read
-- 07/896,160 --

Column 1, line 40; insert the word -- and -- at the end of the line.

Column 2, line 17; delete the "(" at the end of the line leaving the hyphen "-"

Column 2, line 18; insert the "(" at the beginning of the line to make it read -- (triphenylphosphine) --

Column 4, line 68; "(NH$_3$) M+NH$_4$:m/z=176" should read
-- (NH$_3$) M+NH$_4^+$:m/z=176 --

Column 7, line 16; "[e]" should read -- [c] --

Column 7, line 27; "7-(βD-2,3,4,6-" should read
-- 7-(β-D-2,3,4,6- --

Column 7, line 27; insert a "]" at the end of the line before the hyphen "-"

Column 7, line 28; delete the "]" at the beginning of the line.

UNITED STATES PATENT AND TRADEMARK OFFICE
CERTIFICATE OF CORRECTION

PATENT NO. : 5,405,948

DATED : April 11, 1995

INVENTOR(S) : Jean-Marie Beau, Christophe Crevisy, Ghanem Atassi, Alain Pierre

It is certified that error appears in the above-indentified patent and that said Letters Patent is hereby corrected as shown below:

Column 8, line 51, insert the word —and— at the end of the line.

Signed and Sealed this

Twenty-ninth Day of August, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,405,948
DATED : April 11, 1995
INVENTOR(S) : Jean-Marie Beau, Christophe Crevisy, Ghanem Atassi, Alain Pierre It is certified that error appears in the above-indentified patent and that said Letters Patent is hereby corrected as shown below:

Title Page, Item [57] ABSTRACT, line 10: <u>insert</u> the following: -- or, alternatively the group --; <u>also insert</u> a comma -- , -- after the second formula at the end of the line. (Resp. & Amdt. dtd 11/4/93, Pg. 1, line 12.

Column 8, line 67: "bezocyclodeca" should read -- benzo[c]cyclodeca --. (Resp. & Amdt. dtd 4/7/94, Pg. 1).

Signed and Sealed this

Third Day of September, 1996

Attest:

BRUCE LEHMAN

*Attesting Officer*   *Commissioner of Patents and Trademarks*